May 29, 1973 D. L. ARMSTRONG Plant Pat. 3,348
ROSE PLANT
Filed Sept. 30, 1971
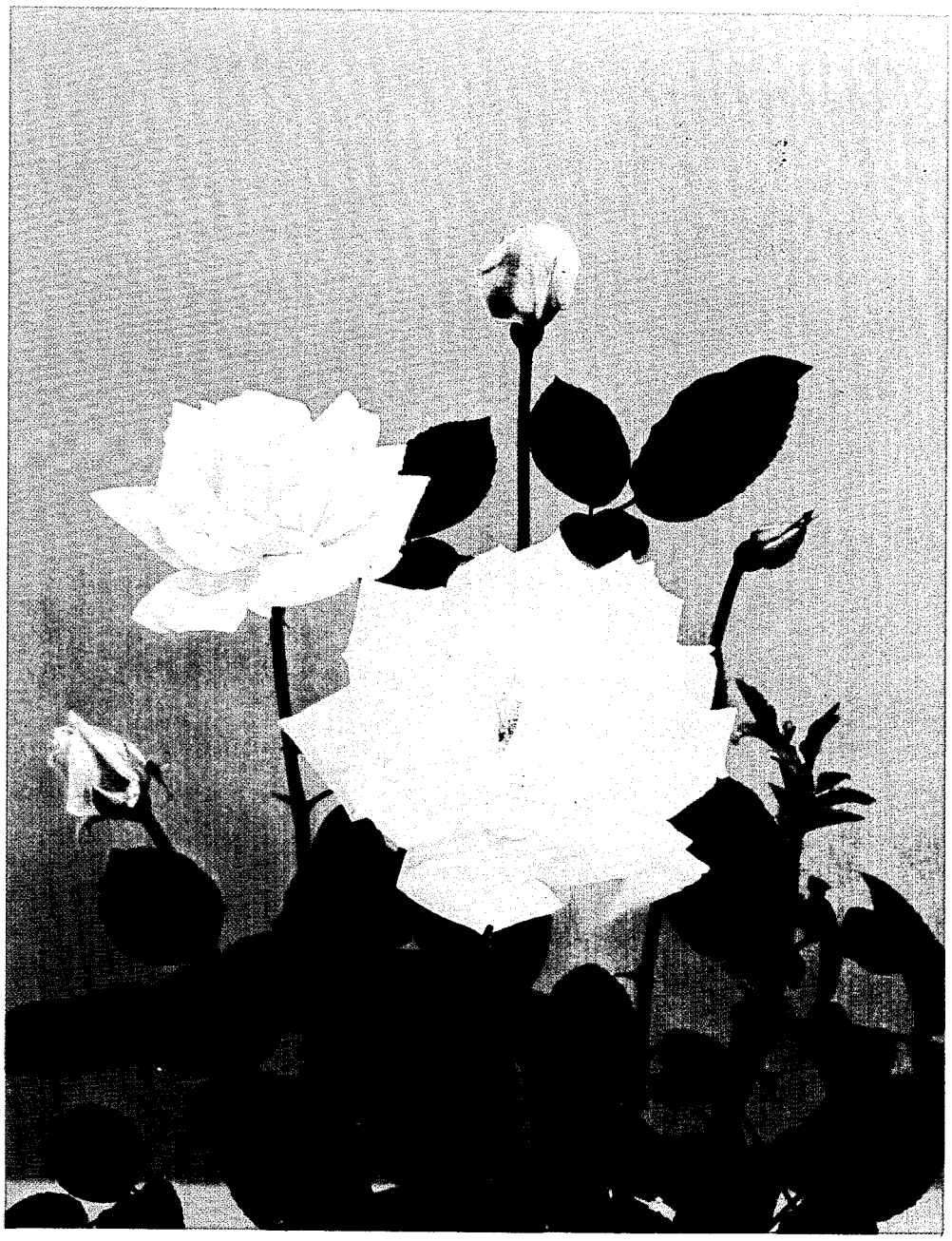

United States Patent Office

Plant Pat. 3,348
Patented May 29, 1973

3,348

ROSE PLANT

David L. Armstrong, Upland, Calif., assignor to Armstrong Nurseries, Inc., Ontario, Calif.

Filed Sept. 30, 1971, Ser. No. 185,455
Int. Cl. A01h 5/00
U.S. Cl. Plt.—15 1 Claim

ABSTRACT OF THE DISCLOSURE

A new variety of rose plant of the Hybrid Tea class, of medium to tall growth habit, vigorous and much branched, with strong moderate length upright stems, usually each bearing only one bloom. The peduncles are unusually strong, and each will hold a fully opened flower in upright position, even though the flowers are relatively large, measuring from 4½" to 7" in diameter.

The buds have foliaceous appendages extending beyond the tip a distance equal to from one-third to full bud length. As the bud opens, the outer surface of the petals displays a deep golden yellow color, heavily overlaid with a strong orangish-red.

The general color effect of the fully opened flower is a creamy yellow, with light orangish-pink overtones. There are from 30 to 40 petals, with 10 to 16 petaloids.

A particularly desirable characteristic is the relative longevity of the flowers, when grown outdoors. On the bush, they last from 5 to 10 days in moderately cloudy weather in southern California. As cut flowers, at living-room temperatures, they will last for from 4 to 7 days. The flower has a pleasing moderately strong fragrance.

This invention relates to a new variety of hybrid tea rose, of the tall, bush type, grown as an outdoor plant for cut flowers and garden decoration. It was propagated and grown in Ontario, Calif.

The plant is a seedling having as its seed parent Manitou, and as its pollen parent Summer Sunshine (Plant Patent 2,078). It holds its distinguishing characteristics through suceeding propagations by budding.

The accompanying drawing illustrates the plant in color and shows the flowering thereof from bud to full bloom.

This new variety may be distinguished from its seed parent, Manitou, in the following characteristics:

The plant of this new variety is taller and more vigorous than the plant of Manitou. The stems of this new variety have more small prickles, especially on the lower one-fourth to one-third of their length, than do the stems of Manitou.

The leaves of this new variety are not as resistant to damage from mildew, however, as the leaves of Manitou. The mature leaflets and leaves of this new variety are generally smaller than the mature leaflets and leaves of Manitou, and have a duller appearance than the leaves of Manitou, which are glossy.

The underside of the rachis of this new variety is usually smooth, whereas on the underside of the rachis of Manitou there are usually many stipitate glands. There may be from none to four small prickles in this location in either variety.

As the calyx breaks, the buds of this new variety are substantially longer in relation to their breadth than are the buds of Manitou. The bud color, as the calyx breaks, ranges from a deep golden yellow color with heavy reddish-orange overcasts to deep reddish-orange, whereas on buds of Manitou in the same stage of development the color is a deep rosy-red.

This new variety is distinguished from its pollen parent, Summer Sunshine, in the following characteristics:

The plant of this new variety is taller and more vigorous, and has a more erect habit of growth, than does the plant of Summer Sunshine.

The flowers of this new variety, usually held upright, are borne on stronger and more erect stems than are the flowers of Summer Sunshine, and whereas Summer Sunshine may occasionally have two or more flowers to the stem, rather than only one, this new variety characteristically has only one flower to the stem and is less often found with more than one flower to the stem.

The peduncles of this new variety are more erect and are of larger caliper than are the peduncles of Summer Sunshine.

The unopen flower buds of this new variety are substantially wider at the base in relation to their length than are the buds of Summer Sunshine before they open. The opening flower buds of this new variety are longer than the opening flower buds of Summer Sunshine.

Whereas Summer Sunshine only occasionally has foliaceous appendages extending beyond the tip of the buds, these extending generally less thane one-half the bud length, the sepals of this new variety more frequently have such appendages, and these may often be as long in extent as the flower bud itself.

The flowers of this new variety are usually significantly larger than the flowers of Summer Sunshine; those of the former ranging in size from 4½ inches to 7 inches when fully opened and those of the latter being from 3½ inches to 5 inches wide when fully opened. The flowers of this new variety characteristically have from 30 to 40 petals plus 10 to 16 petaloids, whereas the flowers of Summer Sunshine have between 22 and 28 petals plus 4 to 8 petaloids.

The flower color of this new variety may be described as being a pale, creamy yellow with light orangish-pink overtones, whereas the flower color of Summer Sunshine is a bright, deep yellow. The flower buds of this new variety, as the calyx breaks, are a deep golden yellow color heavily overlaid with a strong orangish-red, especially on the outer surface of the outside petals, whereas buds of Summer Sunshine are a bright yellow color.

The flowers of this new variety are considerably more fragrant than are the flowers of Summer Sunshine.

The flowers are usually borne singly on normal, medium stems. The plant blooms abundantly, both outdoors and in the greenhouse, and almost continuously during the growing season. The fragrance is moderate.

Throughout this specification, color names beginning with a small letter signify that the name of that color, as used in common speech, is aptly descriptivce. Color names beginning with a capital letter designate values based upon the Nickerson Color Fan, put out by Munsell Color Co.

*Bud*

The peduncle is average length to long, of average caliper, erect and stiff. Its color is near Strong Yellow Green, 5GY 6/8. It is entirely smooth, or may have from a few to numerous stipitate glands and a few small prickles. It may be observed that there are more prickles and stipitate glands on the peduncles of plants grown outdoors than on those which are grown in a greenhouse.

Before the calyx breaks, the bud is medium to large size, medium length, pointed, and with a conspicous neck.

As the calyx breaks, the color is near Strong Greenish Yellow, 10Y 8/11, overlaid with near Strong Red, 5R 4/12.

The inner surface of the sepals is lined with a fine, wooly tomentum. Margins of alternate sepals are lined with a fine, wooly tomentum, the margins of others usually having narrow foliaceous parts and small stipitate glands. The tips of the sepals sometimes have foliaceous appendages. The foliaceous parts generally are larger on plants which are grown outdoors. The outer surface of the sepals is usually smooth.

As the first petal opens, it is average to large in size, being long, and ovoid to urn-shaped in form. The outer surface of the petal is between Strong Orange Yellow, 7.5YR 7/11, and Moderate Orange Yellow, 7.5YR 8/8, overlaid with near Strong Red, 5R 4/12. At the base, near the point of attachment, the petal is near Vivid Greenish Yellow, 7.5Y 8/12. The inner surface is near Vivid Yellow, 2.5Y 8/12, overlaid with near Strong Orange, 2.5YR 6/12.

The bud opens up well, and is not retarded or prevented from opening by cold, hot, wet, or dry weather.

*Bloom*

When fully open, the bloom is average to large in size, being from 4½ inches to 7 inches across. The petalage is double, ranging from 30 to 40 petals, plus 10 to 16 petaloids, which are arranged irregularly on flowers which are grown outdoors.

The form of the bloom is high centered at first, later becoming open and high centered. At first, the petals remain somewhat cupped, with tips reflexed outward; later, at maturity, they are more loosely cupped, with tips rolled outward. The petals are of medium texture, moderately leathery, with both the inside and outside satiny. The shape of all petals is obovate. The colors may be modified by being shaded and/or washed with other colors.

The following description applies to a newly opened flower in the month of April, in Ontario, Calif. The plant was grown in a greenhouse.

The outer surface of the outside petal is near Moderate Orange Yellow, 10YR 8/10, overlaid with near Deep Pink, 2.5R 6/11, with an area at the base near the point of attachment being near Vivid Yellow, 5Y 8/12. The inner surface of the outside petal is between Vivid Yellow, 2.5Y 8/12, and Moderate Orange Yellow, 10YR 8/10. An area at the base near the point of attachment is near Vivid Greenish Yellow, 7.5Y 8/12.

The outer surface of the intermediate petal is near Brilliant Yellow, 2.5Y 9/9, lightly overlaid with near Moderate Pink, 2.5R 8/5, with an area at the base between Brilliant Greenish Yellow, 7.5Y 9/8, and Vivid Greenish Yellow, 7.5Y 8/12. The inner surface of the intermediate petal is near Brilliant Yellow, 5Y 9/9, with an area at the base, near the point of attachment, being near Vivid Greenish Yellow, 7.5Y 8/12.

The outer surface of the inside petal is near Brilliant Yellow, 2.5Y 9/9, very lightly overlaid with near Strong Yellowish Pink, 5R 7/9. The inner surface of the inside petal is between Brilliant Yellow, 2.5Y 9/9, and Brilliant Yellow, 5Y 9/9. An area at the base of both the inner and outer surfaces near the point of attachment is near Vivid Greenish Yellow, 7.5Y 8/12.

The description which follows was made from a rose that was open for three days in a greenhouse in the month of April, in Ontario, Calif.

The outer surface of the outside petal is between White and Pale Orange Yellow, 7.5YR 9/4, very lightly overlaid with near Moderate Pink, 2.5R 8/5. The inner surface of the outside petal is also between White and Pale Orange Yellow, 7.5YR 9/4. An area at the base, near the point of attachment, is near Vivid Greenish Yellow, 7.5Y 8/12, on both the inner and outer surfaces.

The outer surface of the inside petal is near White, i.e., between White and a color lighter than Pale Orange Yellow, 7.5YR 9/4. The inner surface of the inside petal is between White and a color lighter than Brilliant Greenish Yellow, 7.5Y 9/8. An area at the base, near the point of attachment, is near Brilliant Greenish Yellow, 7.5Y 9/8, on both the inner and outer surfaces.

The general color effect of the newly opened flower is between Brilliant Yellow, 2.5Y 9/9, and Brilliant Yellow, 5Y 9/9. After the bloom has been three days open, the color effect is between White and a color lighter than Brilliant Greenish Yellow, 7.5Y 9/8.

The petals drop off cleanly, and are not particularly affected by cold, hot, wet, or dry weather.

The flower persists on the bush in the garden for from five to ten days, in overcast weather, in the month of April. Roses grown outdoors, but cut and kept at living-room temperatures, persist from four to seven days in the month of April.

*Reproductive organs*

Stamens: The stamens are average in number, arranged regularly about the pistils, a few being mixed with petaloids.

Filaments: The filaments are medium length to long, from 9–16 mm. in length. Their color is near Vivid Yellow, 5Y 8/12, some being slightly to much overlaid with near Deep Yellowish Pink, 5R 6/11, and most with anthers.

Anthers: The anthers are large, all opening approximately at once. On the upper side their color is near Strong Orange Yellow, 7.5YR 7/11 on the margins, the remainder being near Brilliant Yellow, 5Y 9/9. On the under side, their color is near Brilliant Yelow, 5Y 9/9.

Pollen: The pollen is moderate in quantity, and is near Moderate Orange Yellow, 7.5YR 8/8, in color.

Pistils: The pistils are average to many in number, there being approximately 90 of them.

Styles: The styles are moderately even, average in length and caliper, and somewhat loosely bunched. Their color is lighter than Brilliant Greenish Yellow, 7.5Y 9/8 becoming near Strong Red, 5R 4/12 near the stigma.

Stigma: The stigma is near Strong Orange Yellow, 7.5YR 7/11, in color.

Ovaries: The ovaries are, for the most part, enclosed in the calyx, although a few protrude.

*Foliage*

The compound leaves usually comprise from 3 to 5 to 7 leaflets, and are abundant. They are medium in size, somewhat leathery, and semi-glossy. The leaflets are ovoid in shape, with apex acute, base round, and margin simply serrate.

The color of the mature foliage on the upper surface is near Grayish Olive Green, 5GY 3/2, when grown outdoors. The under surface is between Moderate Olive Green, 5GY 4/3, and Grayish Olive Green, 5GY 3/2, when grown outdoors.

The young growth, on its upper surface, is near Moderate Yellow Green, 5GY 5/6, overlaid with near Dark Red, 5R 3/7, especially near the margins, when grown in a greenhouse. The undersurface is near Strong Yellow Green, 5GY 6/8, overlaid with near Dark Red, 2.5R 3/7, when grown in the greenhouse.

The rachis is average in size, being grooved on its upper side, with many stipitate glands on the edges. The under side is smooth, with from none to four small prickles.

The stipules are medium-length, narrow, and with medium-length points turning out at an angle of less than 90°.

The plant displays more than average resistance to mildew, when grown outdoors in Ontario, California.

*Growth*

The plant is bushy, upright, and much branched in habit, and free in growth. The canes are from medium to heavy in caliper.

The main stems are near Light Olive, 7.5Y 5/5, in color, some being overlaid with near Dark Red, 2.5R 3/7. They bear several large prickles from medium-length to long, hooked slightly downward, with short to medium-length broad base. There are very few small prickles, but both large and small prickles are between Dark Orange Yellow, 7.5 YR 6/9, and Strong Yellowish Brown, 7.5YR 5/7, in color. There are no hairs.

The branches are the same coloring as the main stems, i.e., near Light Olive, 7.5Y 5/5, with some overlaid with near Dark Red, 2.5R 3/7. They bear several large prickles from medium-length to long, hooked slightly downward, with short to medium-length broad base. There are few to several small prickles, and both large and small prickles are between Dark Orange Yellow, 7.5YR 6/9, and Strong Yellowish Brown, 7.5 YR 5/7. There are no hairs.

New shoots are near Strong Yellow Green, 5GY 7/10, overlaid with near Strong Purplish Red, 10RP 4/12, on the side exposed to sunlight. They carry from few to several large prickles, which are medium-length, straight or hooked slightly downward, and with medium-length, moderately broad base. Their color is near Strong Yellow Green, 5GY 7/10, at the tips, becoming near Strong Purplish Red, 10RP 4/12, at the base. There are many small prickles and many small stipitate glands. There are no hairs.

I claim:

1. A new variety of rose plant of the hybrid tea class, substantially as herein shown and described, said plant further being characterized by a plurality of combinations of features, including a vigorous moderately tall and many branched habit of growth and moderately long stems; buds having foliaceous appendages extending beyond the bud tip a distance equal to from one-third the bud length to the entire bud length; the peduncles being unusually strong and supporting the flowers upright even when in full bloom; the deep golden yellow color overlaid with strong orangish-red of the opening bud; and the general creamy yellow with light orangish-pink overtones of the color effect of the fully opened flower, which ranges from 4½ inches to 7 inches in diameter and has a pleasing, moderately strong fragrance; said plant being further characterized in the longevity of its bloom, when grown outdoors, ranging from 5 to 10 days in moderately cloudy weather in southern California when the bloom is on the bush, and from 4 to 7 days when the bloom is kept at living-room temperatures after cutting.

No references cited.

ROBERT E. BAGWILL, Primary Examiner